(12) United States Patent
Mercereau et al.

(10) Patent No.: US 6,450,937 B1
(45) Date of Patent: Sep. 17, 2002

(54) NEEDLE FOR IMPLANTING BRACHYTHERAPY SEEDS

(75) Inventors: Steven F. Mercereau; Charles Jacobs, both of Conyers, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/466,507

(22) Filed: Dec. 17, 1999

(51) Int. Cl.$^7$ .................................................. A61N 5/10
(52) U.S. Cl. ............................................. 600/7; 604/57
(58) Field of Search .................. 600/1–8; 604/264–266, 604/890.1, 891.1, 272, 110

(56) References Cited

U.S. PATENT DOCUMENTS

| | | |
|---|---|---|
| 4,402,308 A | 9/1983 | Scott |
| 4,453,928 A | 6/1984 | Steiger |
| 4,535,773 A | 8/1985 | Yoon |
| 4,588,398 A | 5/1986 | Daugherty et al. |
| 4,627,841 A | 12/1986 | Dorr |
| 4,697,575 A * | 10/1987 | Horowitz ..................... 600/1.2 |
| 4,700,692 A | 10/1987 | Baumgartner |
| 4,763,642 A | 8/1988 | Horowitz |
| 4,869,717 A | 9/1989 | Adair |
| 5,147,282 A | 9/1992 | Kan |
| 5,242,373 A | 9/1993 | Scott et al. |
| 5,312,345 A | 5/1994 | Cole |
| 5,334,159 A | 8/1994 | Turkel |
| 5,470,318 A | 11/1995 | Griffith, III et al. |
| 5,487,739 A | 1/1996 | Aebischer et al. |
| 5,540,662 A | 7/1996 | Nicholson |
| 5,860,909 A | 1/1999 | Mick et al. |
| 5,906,574 A | 5/1999 | Kan |
| 5,911,711 A | 6/1999 | Pelkey |
| 5,928,130 A | 7/1999 | Schmidt |
| 5,938,583 A | 8/1999 | Grimm |
| 5,997,463 A | 12/1999 | Cutrer |
| 6,123,700 A * | 9/2000 | Mills et al. .............. 604/890.1 |

FOREIGN PATENT DOCUMENTS

| | | |
|---|---|---|
| WO | PCT 98/01179 | 1/1998 |
| WO | PCT 99/42149 | 8/1999 |

* cited by examiner

*Primary Examiner*—Eric F. Winakur
*Assistant Examiner*—Nikita R Veniaminov
(74) *Attorney, Agent, or Firm*—Kilpatrick Stockton LLP

(57) ABSTRACT

A brachytherapy needle for delivering radioactive seeds into the body of a patient comprises a tube into which the radioactive seeds and intervening spacers are loaded. The tube is telescopically disposed within a cutting cannula and is substantially longer than the cannula such that the cannula can be withdrawn over the tube, leaving the forward end of the tube exposed within the tissues of the patient. When the cannula is retracted, the seeds within the tube can be visualized using conventional medical imaging technology. The tube of the disclosed embodiment includes a deformable constriction which normally retains the seeds within the lumen of the needle but which deforms to permit the seeds to pass when subjected to a predetermined force. The tube of the disclosed needle has a low-friction exterior surface to prevent tissue from being displaced as the device is withdrawn. In yet another aspect the cannula and telescoping hollow tube are dimensioned such that when the cannula is withdrawn with respect to the tube, the blunt forward edge of the tube extends beyond the cutting edge of the hollow cannula to prevent accidental needle sticks.

24 Claims, 5 Drawing Sheets

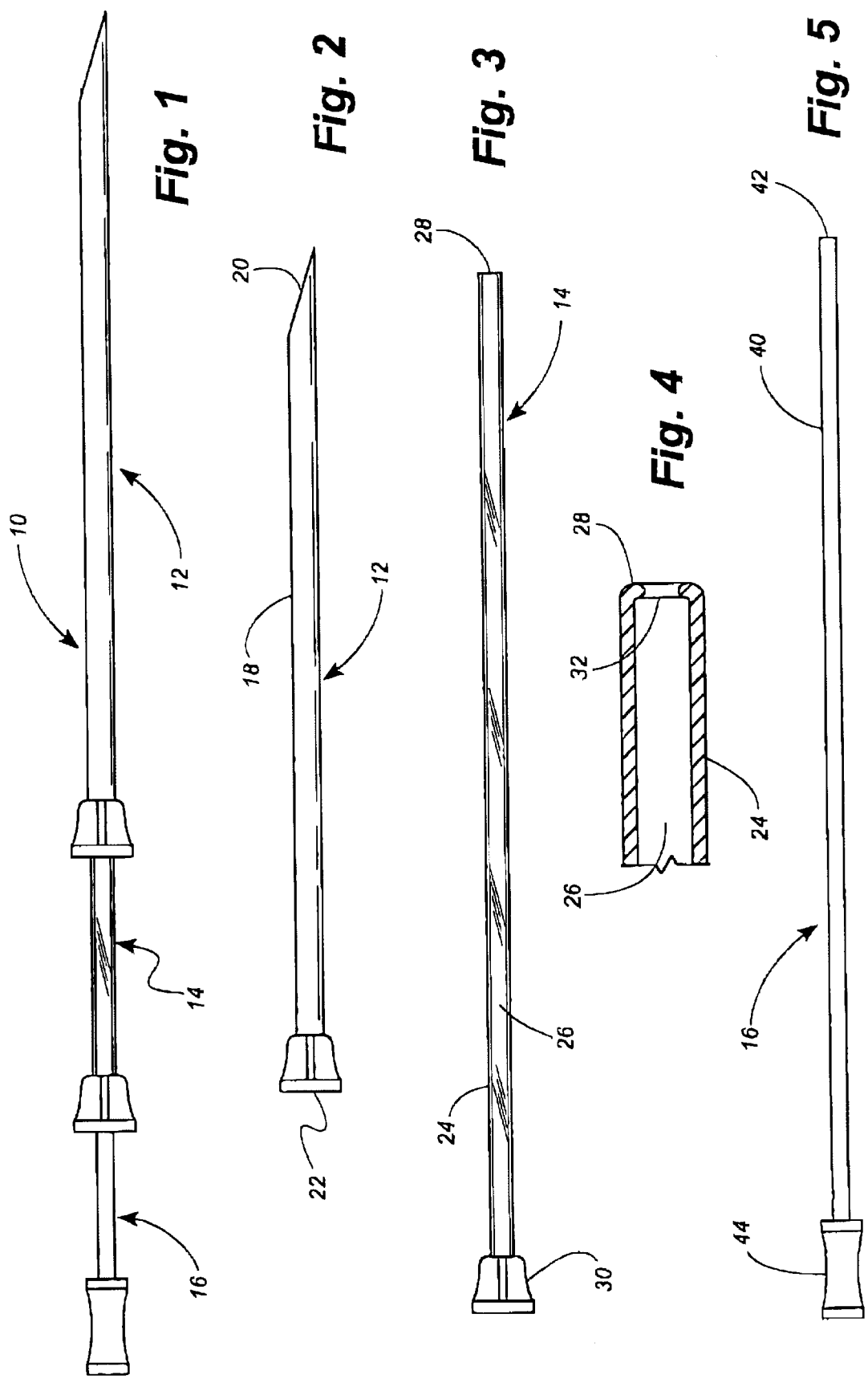

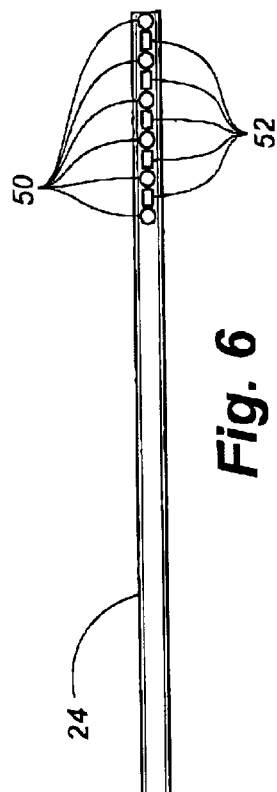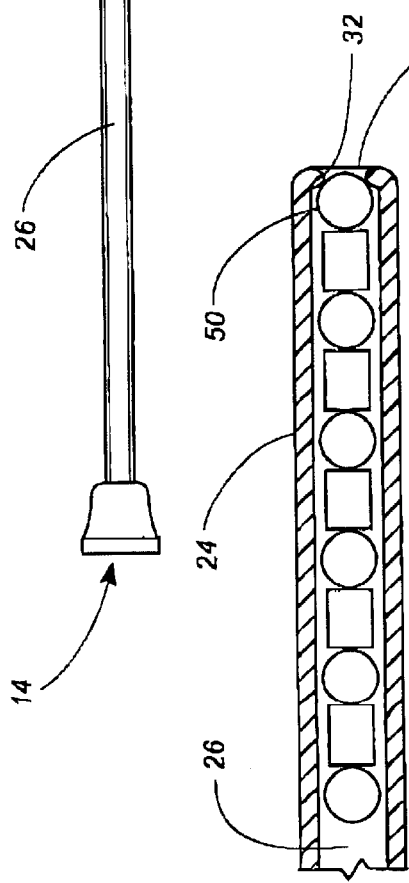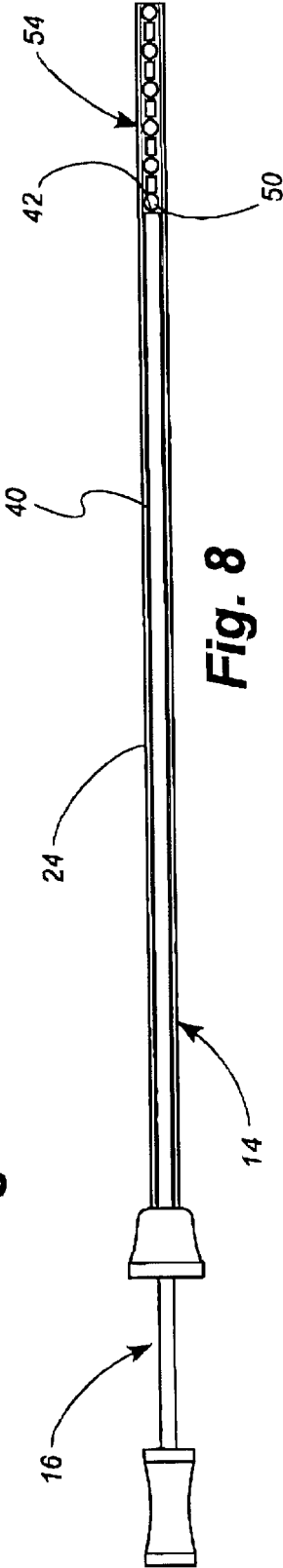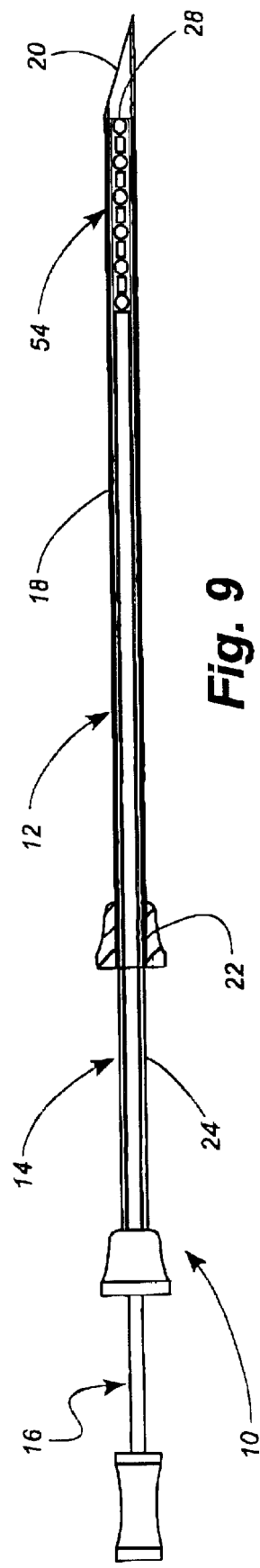

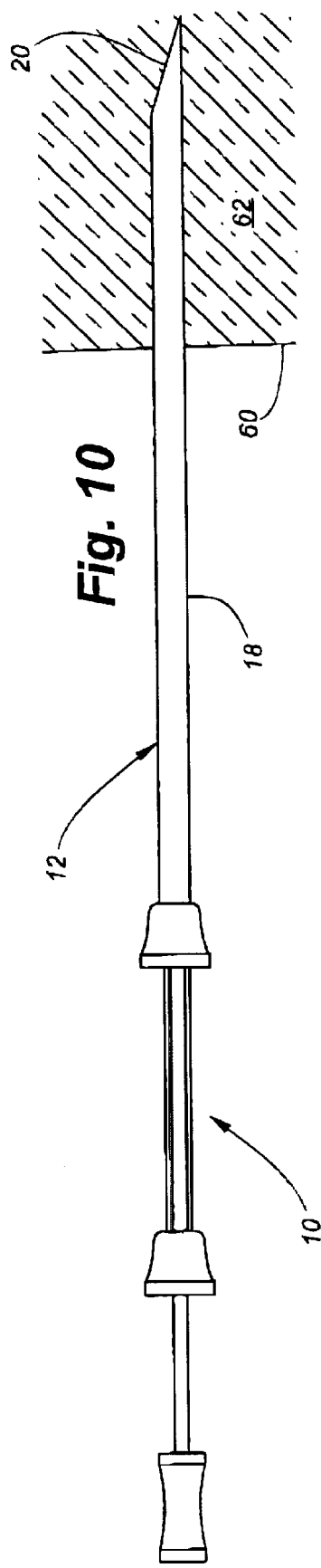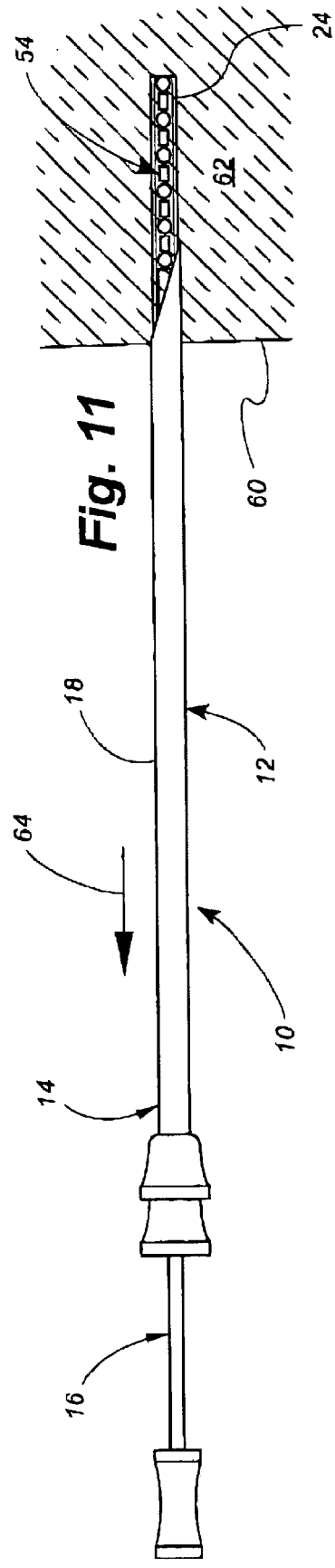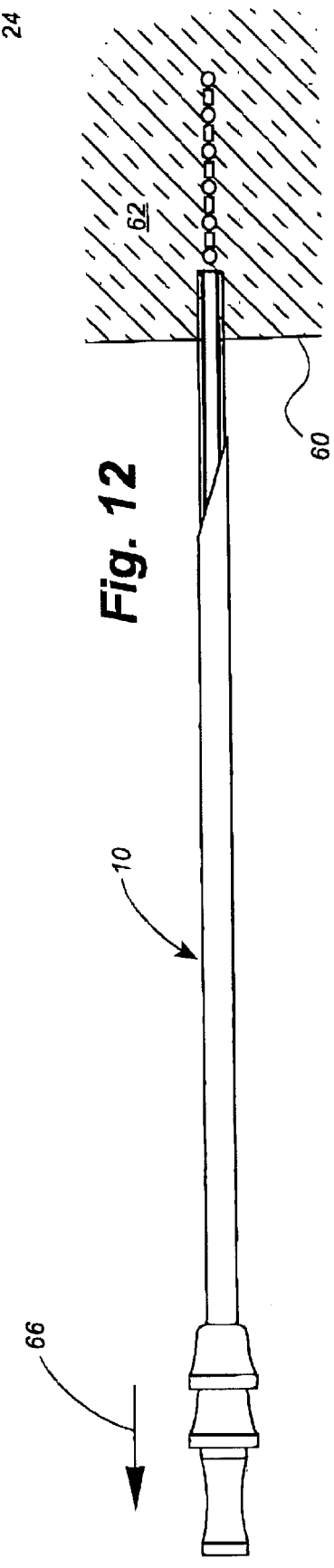

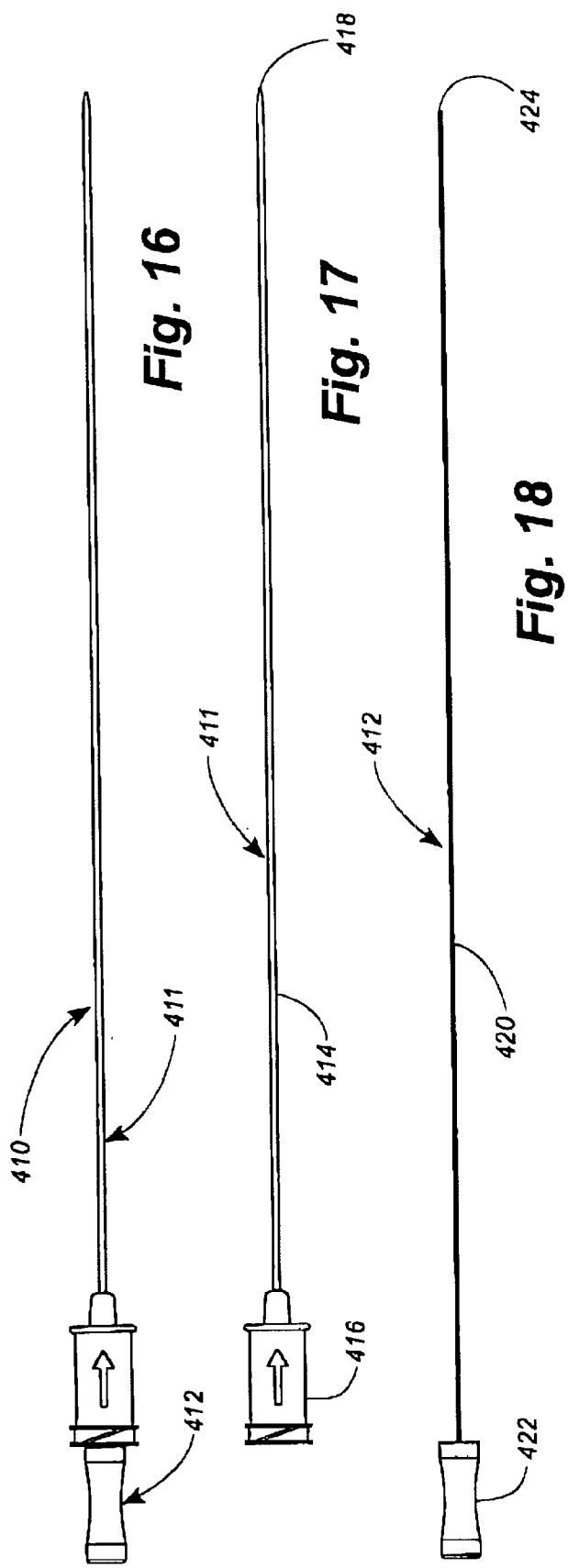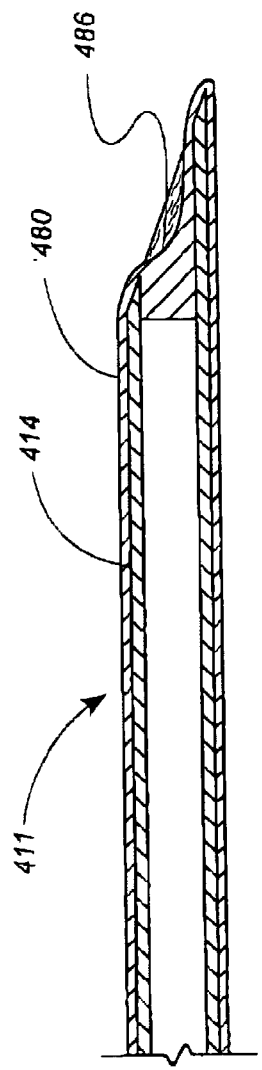

NEEDLE FOR IMPLANTING BRACHYTHERAPY SEEDS

TECHNICAL FIELD

The present invention relates generally to surgical devices for implanting substances within the body of a patient for therapeutic purposes. More specifically the present invention relates to a needle for implanting radioactive seeds within the body of a patient for localized radiation treatment of a tumor.

BACKGROUND OF THE INVENTION

It is well known to treat tumors with localized radiation by implanting radioactive seeds within the body of the patient within or in the vicinity of the tumor. The seeds typically comprise I-125, Pd-103, or other suitable radioactive agent contained within a pellet or seed to prevent migration of the radioactive material throughout the body of the patient.

Such radioactive seeds, known as "brachytherapy" seeds, are conventionally implanted within the body of the patient by advancing the seeds through a hollow needle or "stylet" with a push rod or cannula. Since it is usually desirable to implant a number of seeds in a single procedure, a plurality of seeds can be loaded into the stylet. To assure proper spacing between adjacent seeds, spacers of cat gut or other bioabsorbable material may be placed between adjacent seeds. The needle is then inserted into the body of the patient to a location adjacent the tumor. The physician then holds the cannula steady as the stylet is withdrawn, pushing the seeds and spacers out into the tissues of the patient as the stylet is retracted.

Conventional brachytherapy seed needles suffer a number of disadvantages. Because the seeds are housed within the forward end of a steel needle when inserted into the tissues of the patient, it is not possible to visualize the exact position of the seeds using ultrasound or other medical imaging technology. Accordingly there is a need for a needle for implanting brachytherapy seeds which permits the location of the seeds to be visualized by medical imaging technology prior to the seeds being deployed.

Another problem concerns a means for retaining the seeds in the forward end of the needle. To prevent the seeds from falling out of the needle, the forward end of the needle must be closed, such as with a plug of a biodegradable material. Thus, when the brachytherapy seeds are pushed out into the patient, the plug is also pushed out into the patient and remains in the patient. It would thus be desirable if there were a brachytherapy needle which did not require to prevent the seeds from falling out a plug which would be implanted into the patient's body along with the seeds.

The number and location of brachytherapy seeds used in a given treatment is carefully calculated to deliver a predetermined dose of radiation to the tumor. Since the amount of radiation delivered to a tumor depends upon the spacing and location of the seeds relative to the tumor, optimal brachytherapy treatment requires careful positioning of the seeds. A problem associated with prior art brachytherapy procedures is that friction between the brachytherapy needle and the tissues of the patient can cause the seeds to be improperly positioned. More specifically, as the cannula of the brachytherapy needle is retracted to expose the seeds in the tissues of the patient, friction between the outer surface of the cannula and the patient's tissues causes the tissues to distend. The seeds are deployed into the distended tissue. When the frictional force is removed, the tissue subsequently returns to its normal position, causing the seeds to be displaced as the tissue moves. The seeds may thus not be positioned in the desired locations. Thus there is a need for a way to reduce or eliminate the effect of friction between the brachytherapy needle and the surrounding tissue as the seeds are being implanted.

Finally, after the procedure is finished, the brachytherapy needle itself becomes a biohazard. The sharp tip of the cannula lends itself to accidental needle sticks. Thus there is a further need for a brachytherapy seed needle which minimizes the possibility of accidental needle sticks.

SUMMARY OF THE INVENTION

Stated generally, the present invention comprises an improved needle for implanting radioactive seeds which addresses each of the disadvantages associated with conventional brachytherapy needles. The brachytherapy needle of the present invention permits the radioactive seeds to be visualized using medical imaging technology prior to the seeds being discharged from the needle. Thus the needle can be repositioned if necessary for accurate placement of the seeds. In a disclosed embodiment the needle also retains the seeds within the needle without the need for a plug which will be left within the patient's body. In one aspect of the invention the needle substantially eliminates the possibility of the brachytherapy seeds being improperly placed as a result of friction between the needle and the surrounding tissue distending the tissue as the needle is withdrawn. And the design of the needle of the disclosed embodiment is such that, after normal use, the cutting forward edge of the needle is shielded without any active intervention on the part of the physician to prevent accidental needle sticks.

Stated somewhat more specifically, the present invention relates to a brachytherapy needle in which radioactive seeds are delivered into the body of a patient by pushing them with a stylet through a hollow tube. In a first aspect the needle assembly of the present invention comprises a transparent or translucent tube into which the radioactive seeds and intervening spacers are loaded, such that the seeds and spacers can be seen within the tube. The physicist who loads the seeds, the radiation oncologist, and the urologist thus all have the option of visually inspecting the tube to insure that the seeds are properly loaded.

In another aspect the needle assembly of the present invention comprises a tube into which the seeds are loaded and which is telescopically disposed within a cutting cannula. The tube is substantially longer than the cannula such that the cannula can be withdrawn over the tube, leaving the forward end of the tube exposed within the tissues of the patient. The tube is formed from a material which is transparent to the medical imaging modality being used. When the cannula is retracted, the seeds within the tube can be visualized within the tissues of the patient using conventional medical imaging technology.

In another aspect the needle of the present invention includes a deformable constriction which retains the seeds within the lumen of the needle against the force of gravity but which deforms to permit the seeds to pass when subjected to a force greater than the force of gravity.

In still another aspect the needle of the present invention has a low-friction exterior surface to prevent tissue from being displaced as the needle is withdrawn. In one disclosed embodiment the tube has a low-friction coating applied to its exterior surface. Coating material is permitted to accumulate within the forward end of the tube, thereby forming a deformable constriction which retains the seeds within the lumen of the needle against the force of gravity but which deforms to permit the seeds to pass when subjected to a force greater than the force of gravity.

Another aspect of the invention relates to a conventional two-piece cannula and stylet brachytherapy needle design. The novel feature is a low-friction coating applied to the exterior surface of the cannula. Coating material is permitted to accumulate within the forward end of the cannula, thereby forming a deformable constriction which retains the seeds within the lumen of the cannula against the force of gravity but which deforms to permit the seeds to pass when subjected to a force greater than the force of gravity.

In yet another aspect the needle of the present invention comprises a cannula and a hollow tube in telescoping relation, the cannula and tube being dimensioned such that when the cannula is withdrawn with respect to the tube, the blunt forward edge of the tube extends beyond the cutting edge of the hollow cannula to prevent accidental needle sticks.

BRIEF DESCRIPTION OF THE DRAWINGS

FIG. 1 is a side view of a needle assembly for implanting brachytherapy seeds according to the present invention.

FIG. 2 is a side view of a cannula of the needle assembly of FIG. 1.

FIG. 3 is a side view of a seed carrier of the needle assembly of FIG. 1.

FIG. 4 is an enlarged cross sectional view of the forward end of the seed carrier of FIG. 3.

FIG. 5 is a side view of a push stylet of the needle assembly of FIG. 1.

FIG. 6 is a side view of the seed carrier of FIG. 3 showing a plurality of radioactive seeds and intervening spacers loaded in the forward end of the seed carrier.

FIG. 7 is an enlarged cross sectional view of the forward end of the seed carrier of FIG. 6.

FIG. 8 shows the loaded seed carrier of FIG. 6 with the push stylet of FIG. 5 telescopically received within the seed carrier.

FIG. 9 shows the seed carrier and stylet assembly of FIG. 8 telescopically received within the cannula of FIG. 2, with the cannula shown in cross section to reveal interior detail.

FIGS. 10–12 illustrate the sequence of steps by which the loaded needle assembly of FIG. 9 is used to implant radioactive seeds within the tissues of a patient, where:

FIG. 10 shows the forward end of a needle assembly inserted into the tissues of a patient;

FIG. 11 shows the cannula retracted with respect to the seed carrier to expose the forward end of the seed carrier within the tissues of the patient; and FIG. 12 shows the seed carrier and cannula retracted with respect to the push stylet to expose the radioactive seeds and spacers within the tissues of the patient.

FIG. 16 is a top view of a second embodiment of a needle assembly for implanting brachytherapy seeds according to the present invention.

FIG. 17 is a top view of a cannula of the needle assembly of FIG. 16.

FIG. 18 is a side view of a stylet of the needle assembly of FIG. 16.

FIG. 19 is an enlarged cross-sectional schematic representation of the forward end of the cannula of FIG. 17.

DETAILED DESCRIPTION OF THE DISCLOSED EMBODIMENT

Figure 13:
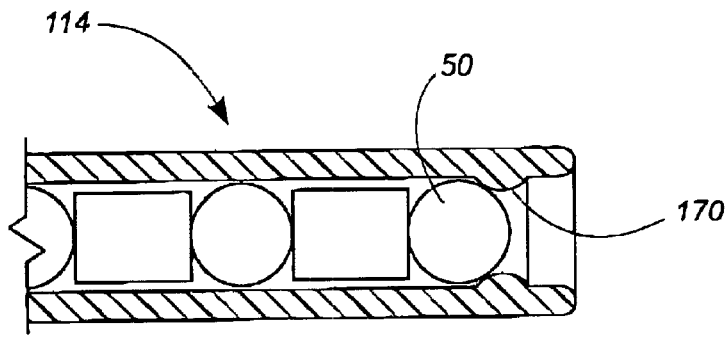
FIG. 13 is a cross-sectional view of the forward end of a first alternate embodiment of a seed carrier.

Referring now in more detail to the drawings, in which like numerals indicate like elements throughout the several views, FIG. 1 illustrates a needle assembly 10 according to a disclosed embodiment of the present invention. The needle assembly 10 comprises three elements: a hollow cannula 12, a seed carrier 14 telescopically received within the cannula 12, and a push stylet 16 telescopically received within the seed carrier 14. Each of these components will now be discussed in more detail.

Referring now to FIG. 2, the cannula 12 comprises a hollow needle 18 formed from stainless steel or other suitable material. A beveled cutting edge 20 is formed at the forward end of the needle 18. A needle head 22 is located at the rearward end of the needle 18. The needle head 22 provides a convenient means by which a physician may grasp and manipulate the cannula 12. In the disclosed embodiment the needle head 22 of the cannula 12 is approximately 1.75 centimeters in length, and the exposed shaft of the hollow needle 18 is approximately 15 centimeters long.

As shown in FIG. 3, the seed carrier 14 comprises an elongated hollow tube 24 formed from a transparent or translucent material such as nylon, Teflon, or a polycarbonate or mixtures thereof. Essentially any material which is transparent or translucent to allow visualization of the interior of the tube and which is substantially transparent to the applicable imaging modality would provide satisfactory results. The outer diameter of the tube 24 is slightly smaller than the inner diameter of the hollow cannula needle 18. The tube 24 defines a lumen 26 therethrough. The forward end 28 of the tube 24 is blunt. A needle head 30 is formed at the rearward end of the tube 24 and provides a means by which the physician may grasp and manipulate the seed carrier 14. As can be seen in FIG. 4, the forward end 28 of the tube 24 has an inwardly projecting circumferential lip 32 which partially constricts the forward end of the lumen 26. In the disclosed embodiment the needle head 30 of the seed carrier 14 is approximately 2.25 centimeters in length, and the exposed portion of the tube 24 is approximately 24 centimeters in length.

Referring now the to FIG. 5, the push stylet 16 includes an elongated rod 40 formed of stainless steel or other suitable material. The outer diameter of the rod 40 is slightly smaller than the inner diameter of the tube 24 of the seed carrier 14. The forward end 42 of the rod 40 of the push stylet 16 is blunt, and a needle head 44 is formed at the rearward end of the rod. Again, the needle head 44 provides a convenient means by which a physician may grasp and manipulate the push stylet. In the disclosed embodiment the needle head 44 of the push stylet 16 is approximately 1.75 centimeters in length, and the exposed portion of the rod 40 is approximately 26.25 centimeters in length. The length of the rod 40 in the disclosed embodiment is selected to correspond to the overall length of the seed carrier 14 (2.25 centimeters for the needle head 30, 24 centimeters for the tube 24). Thus when the push stylet 16 is fully advanced into the seed carrier 14 such that the forward end of the stylet needle head 44 abuts the rear end of the seed carrier needle head 30, the forward end 42 of the rod 40 of the push stylet extends to the forward end 28 of the tube 24.

Preparation of the needle assembly 10 for use will now be discussed with reference to FIGS. 6–9. Referring first to FIG. 6, radioactive seeds 50 and intervening spacers 52 are loaded into the rearward end of the seed carrier 14 and advanced until the front seed impinges upon the circumferential lip 32 at the forward end 28 of the tube 24. As can be seen in FIG. 7, the circumferential lip 32 forms an opening in the distal end of the tube 24 having a diameter which is smaller than the diameter of the seeds 50 such that the seeds normally cannot pass out of the forward end 28 of the tube 24. Upon completion of the loading procedure, a column 54 of seeds 50 and spacers 52 is disposed within the forward portion of the tube 24.

Referring now to FIG. 8, the blunt forward end 42 of the rod 40 of the push stylet 16 is inserted into the rearward end of the tube 24 of the seed carrier 14 and advanced until the forward end of the rod contacts the rearmost radioactive seed 50. The column 54 of seeds and intervening spacers is now contained within the forward portion of the tube 24 of the seed carrier 14, prevented from moving forward by the inwardly extending circumferential lip 32 of the tube (FIG. 7), and prevented from moving rearward by the forward end 42 of the stylet rod 40.

With the column 54 of seeds and spacers thus loaded and the seed carrier 14 and push stylet 16 thus assembled, the forward end 28 of the tube 24 is inserted into the rearward end of the cannula 12. The seed carrier 14 is advanced until the forward end of the tube 24 resides within the forward end of the cannula needle 18, as shown in FIG. 9. The cannula needle head 22 exerts a friction fit against the outer circumference of the tube 24 of the seed carrier 14 to prevent the seed carrier from sliding freely within the cannula 12. The friction fit can be overcome by exerting a predetermined longitudinal force between the cannula needle 18 and the tube 24. The needle assembly 10 is now ready for use.

In the disclosed embodiment the tube 24 of the seed carrier 14 is 24 centimeters long, while the overall length of the cannula is only 16.75 centimeters long (15 centimeters for the needle 18, 1.75 centimeters for the needle head 22). Thus when the cannula 12 is fully retracted on the tube 24 of the seed carrier 14, approximately one-third of the length of the tube is exposed. As will be appreciated, the number of seeds 50 and spacers 52 and the length of the spacers can vary widely depending upon the patient. Further, depending upon the procedure, a column 54 of seeds and spacers will typically include three to five seeds and range from 1 to 7 centimeters in length. Thus when the cannula 12 is fully retracted, the portion of the tube 24 which is exposed beyond the forward end of the needle 18 will be of sufficient length to contain a typical column 54 of seeds 50 and spacers 52.

Use of a needle assembly 10 to implant a column 54 of radioactive seeds and spacers into the tissues of a patient will now be explained with reference to FIGS. 10–12. First the needle assembly 10 is loaded and assembled as described above with respect to FIGS. 6–9. Then the forward end of the needle assembly 10 is inserted through the skin 60 of the patient, as shown in FIG. 10, and advanced through the tissues 62 to a location adjacent the target site. The cutting forward edge 20 of the cannula needle 18 pierces the tissues 62, and the forward end 28 (not shown in FIG. 10, but see FIG. 9) of the tube 24 is located within the forward end of the cannula needle 18 to prevent the cannula 12 from coring the tissues of the patient.

Next, as shown in FIG. 11, the cannula 12 is retracted with respect to the seed carrier 14 and push stylet 16 in the direction indicated by the arrow 64. Retracting the cannula 12 exposes the forward portion of the tube 24 containing the column 54 of radioactive seeds and spacers within the tissues 62 of the patient. With the column 54 of radioactive seeds and spacers no longer housed within the metal cannula needle 18, location of the seeds within the tissues 62 of the patient can be verified by ultrasound or other medical imaging technology.

Next, as shown in FIG. 12, while the push stylet 16 is held steady, the cannula 12 and seed carrier 14 together are retracted over the rod 40 of the push stylet, as indicated by the arrow 66. As the seed carrier 14 is retracted, the stylet rod 40 prevents the column 54 of seeds and spacers from being withdrawn along with the seed carrier. When the foremost radioactive seed in the column 54 exerts a slight force against the circumferential lip 32 at the forward end of the tube 24, the lip deflects or deforms, and the seed is permitted to move past the constriction. As the tube 24 continues to be withdrawn, the subsequent spacers and seeds in the column 54 are pushed past the constriction at the forward end of the tube and are deployed within the tissues 62 of the patient.

At least the forward portion of the outer surface of the tube 24 of the seed carrier 14 is lubricious. Thus as the tube 24 is withdrawn, friction between the tube and the surrounding tissue 62 is minimal, such that the tissue is not tugged or displaced by the retraction of the tube. This feature eliminates the problem of the seeds 50 being deployed within displaced tissue which subsequently returns to its normal position and displaces the seeds from their intended location.

From the foregoing description it can be seen that each of the three primary components of the needle assembly 10—the cannula 12, the seed carrier 14, and the push stylet 16—has specific functions. The cannula 12 provides a stable shaft for tissue penetration and a cutting point for penetrating the tissue. The cannula 12 also acts as an access conduit for the seed carrier 14 to the target site. The cannula 12 may have echogenic or fluoroscopic properties for easy visualization under ultrasound or other medical imaging technology. Once the seed carrier 14 is in place, however, the cannula 12 can be retracted to provide unobstructed visualization of the forward end of the seed carrier and the seeds 50 and spacers 52 therewithin prior to deployment. In the disclosed embodiment the needle 18 of the cannula 12 is approximately 15 centimeters long. However, it will be understood that the length of the cannula can be selected depending upon the particular location within the patient's body where the seeds 50 are to be implanted. When implanting seeds 50 within the prostate, for example, a typical length between the perineum and the front lobe of the prostate is approximately 17 centimeters, so a slightly longer cannula needle 18 may be required.

The seed carrier 14 has the following functions. The seed carrier fits and smoothly reciprocates within the cannula 12. The seed carrier 14 also functions to hold the contents of the needle assembly 10 prior to deployment. The smooth, lubricious outer surface of the tube 24 of the seed carrier 14 minimizes tissue adherence during movement of the seed carrier. Similarly the smooth, lubricious inner surface of the tube 24 minimizes material adherence between the tube and the rod 40 of the push stylet 16 and between the tube and the seeds 50 and spacers 52. A constriction such as the inwardly projecting circumferential lip 32 can be formed at the forward end 28 of the tube 24 to help retain the contents of the needle assembly 10 while permitting the passage of the contents during deployment. Finally the tube 24 is formed from a material which is transparent or translucent under medical imaging technology to permit direct visualization of the contents of the needle assembly 10 when the cannula 12 is retracted.

The length of the tube 24 of the seed carrier 14 depends upon the length of the cannula 12 with which the seed carrier is used. The tube 24 of the seed carrier 14 should be of sufficient length that when the cannula 12 is fully retracted with respect to the seed carrier, the length of the forward portion of the tube containing the column 54 of seeds and spacers will extend beyond the forward end of the cannula needle 18. Assuming a seed column 54 of 7 centimeters, for example, the tube 24 of the seed carrier 14 would need to be at least 7 centimeters longer than the overall length of the cannula 12.

The function of the push stylet 16 is to fit within and smoothly reciprocate with respect to the seed carrier 14. The rod 40 of the push stylet 16 serves as a piston to push the contents of the seed carrier 14 out of the forward end of the needle assembly 10 and prevents the contents from spilling out the rearward end of the seed carrier. The length of the rod 40 of the push stylet 16 should be selected so that the forward end 42 of the rod will reach the forward end 28 of the tube 24 of the seed carrier 14. Ideally the length of the rod 40 should be selected such that when the push stylet 16 is fully advanced with respect to the seed carrier 14, the forward end 42 of the rod will reach the forward end 28 of the tube 24 of the seed carrier but no further.

In summary, the lengths of the components of the needle assembly 10 are selected as follows. The length of the cannula needle 18 is selected first to provide a suitable length for reaching the target site. The length of the tube 24 of the seed carrier 14 is then selected such that when the cannula 12 is fully retracted with respect to the seed carrier, the forward portion of the tube containing the column 54 of seeds and spacers is fully exposed beyond the forward end of the cannula needle 18. The length of the rod 40 of the push stylet 16 is then selected such that the forward end 42 of the rod will reach the forward end 28 of the tube 24 of the seed carrier 14.

The needle assembly 10 of the disclosed embodiment can be used in various procedures for delivering various materials. For example, brachytherapy for treatment of prostate cancer utilizes needles to deliver radioactive seeds into the prostate. These seeds are delivered through an array of needles that are placed into the prostate in a two axis (x, y) or grid-like fashion to deploy a nest of seeds arranged so that a radioactive dose is delivered throughout the prostate in a prescribed amount. Typically, a seed loader/physicist loads each uniquely identified needle assembly 10 (e.g., column "x," row "y," etc.) with seeds 50 and spacers 52. The column of seeds 50 and spacers 52 in each needle creates the third axis (z) or volume dimension to the nest. It is very important to accurately place seeds and spacers in each needle to assure that each coordinate (x, y, z) is correct and that each seed 50 will be deployed into the proper space to achieve the conformal dose.

Once the needle assemblies 10 are loaded they are arranged in a holder that has the grid coordinates. Each needle is placed in the correct hole (x, y) according to the dose plan. This holder is delivered to the radiation oncologist, who works with the urologist to place each needle into the target prostate. This is done through a template with the grid coordinate fixed next to the patient's perineum. Each needle is inserted into the patient to the proper depth and the seeds are then deployed as described above.

The needle assembly 10 may also be used to implant other objects within the body of a patient. Thermoseeds—small metallic seeds placed within the body of a patient which heat up when exposed to a magnetic field to deliver hyperthermia treatment to tumors—are an example of another object which can be deployed using the needle assembly 10.

As can be seen, the needle assembly 10 provides a number of advantages over prior art needle assemblies for implanting brachytherapy seeds. In conventional brachytherapy needle assemblies a plug of bone wax, anusol, or other biocompatible material must be inserted into the forward end of the needle to prevent the seeds from falling out. Because the tube 24 of the disclosed embodiment is provided with an inwardly extending circumferential lip 32 at its forward end 28, the seeds 50 and spacers 52 are contained within the forward end of the needle assembly 10 without the need for a plug or other retention element which would be deployed along with the seeds and spacers and remain within the tissues of the patient.

Another feature of the invention is the provision of a cannula 12 which is shorter than the seed carrier 14, such that the cannula can be retracted to expose the forward end of the tube 24 within the tissues of the patient. This feature permits the location of the seeds 50 and spacers 52 to be verified by ultrasound or other medical imaging technology after the needle is in the tissues of the patient, an advantage which cannot be realized if the seeds are concealed within the forward end of a metal cannula.

Yet another advantage of having a seed carrier 14 which is longer than the cannula 12 is that after the needle assembly 10 has been used, the blunt forward end 28 of the tube 24 extends beyond the cutting edge 20 at the forward end of the cannula needle 18. This configuration provides a safety advantage, in that anyone accidentally contacting the forward end of a used needle assembly 10 will touch the blunt forward end 28 of the tube 24, rather than the sharp forward cutting edge 20 of the cannula needle 18. The possibility of accidental needle sticks is therefore substantially eliminated. In the disclosed embodiment the stylet and seed carrier extend approximately 8 centimeters beyond the forward tip 20 of the cannula 12.

Still another feature of the needle assembly 10 is the provision of a tube 24 comprised of a translucent or transparent material. The advantage of this feature is that the physicist loading the seeds 50 and intervening spacers 52 into the seed carrier 14 can visually verify proper loading of the needle assembly 10 after the loading sequence has been completed. Thus if the physicist becomes distracted and inadvertently two seeds 50 or two spacers 52 in sequence, the error can be visually detected and remedied prior to use of the needle assembly 10. Further visual inspections may be performed at any time prior to seed deployment, i.e., the loader/physicist, the radiation oncologist, and the urologist each have the option to visually verify proper needle loading.

Another feature of the needle assembly 10 of the disclosed embodiment is the provision of a seed carrier 14 having a lubricious surface which minimizes friction between the seed carrier and the surrounding tissue. The advantage of this feature is that, when the seed carrier 14 is withdrawn, the surrounding tissue will not adhere to the tube 24 of the seed carrier and become distended, thereby causing the seeds 50 to be deployed into tissue which will subsequently move when the friction is released, thereby causing improper location of the seeds. The lubricious outer surface can be achieved by forming the seed carrier 14 from a lubricious material or by placing a lubricious coating on a tube formed from a non-lubricious material.

Modifications and variation on the needle assembly 10 of the disclosed embodiment will immediately be apparent to those skilled in the art. For example, means other than the inwardly extending circumferential lip 32 may be provided for constricting the diameter of the seed carrier 14 to prevent the seeds from falling out of the forward end 28 of the seed carrier. One or more resilient flaps extending at least partially over the opening at the forward end of the tube 10 can be used in lieu of an inwardly extending circumferential lip.

Figure 14:
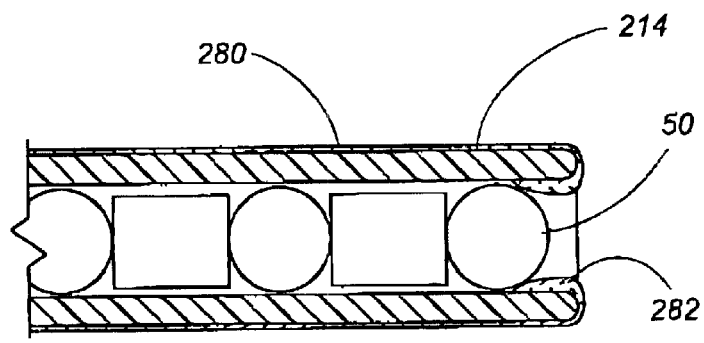
FIG. 14 is a cross-sectional view of the forward end of a second alternate embodiment of a seed carrier.
Figure 15:
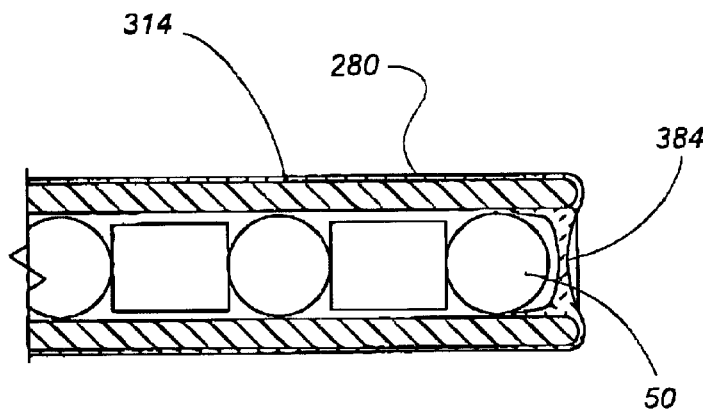
FIG. 15 is a cross-sectional view of the forward end of a third alternate embodiment of a seed carrier.

Still other arrangements for constricting the diameter of a seed carrier are illustrated in FIGS. 13–15. In FIG. 13, the tube of a seed carrier 114 is formed with a portion 170 of reduced diameter. The diameter of the reduced portion 170 is sufficiently small to prevent the seeds 50 from passing under force of gravity, but the seeds can be forced past the reduced portion by advancing the push stylet 16.

Whereas the seed carriers 14, 114 of the embodiments of FIGS. 1–13 are formed from a lubricious material, the seed carriers 214, 314 of FIGS. 14 and 15 are formed from a non-lubricious material having a lubricious coating 280 applied to their outer surfaces. Polyurethanes, polyvinyls, latex, Teflon type materials (e.g., PTFE, TFE), polyethers, polyethylenes, and polyolefms are possible lubricious coatings. In general, any solid polymer that can be carried in a volatile organic solvent can probably be used as a coating. As will be appreciated by those skilled in the art, the temperature and pressure of the solvent and the drying environment may affect the suitability of a particular material to be used as a lubricious coating.

Generally speaking, a known problem in the medical device arts with applying a coating to a hollow tube is the tendency of the coating material to enter the lumen of the tube and clog it. This tendency is used to advantage in the embodiments of FIGS. 14 and 15. Referring first to FIG. 14, the lubricious coating 280 coats not only the outer periphery of the seed carrier 214 but also coats the forward end of the interior of the tube. The coating material 280 is permitted to accumulate at the forward end of the tube and, when cured, forms an inwardly extending circumferential bead 282 which constricts the forward end of the tube. This circumferential bead 282 prevents the seeds 50 from falling out of the forward end of the seed carrier 214 under force of gravity, but the seeds can be pushed past the constriction by the push stylet 16.

In FIG. 15 surface tension has caused the coating material 280 to block the forward end of the tube carrier completely. A web 384 of coating material will prevent seeds 50 from falling out of the forward end of the seed carrier 314 under force of gravity. However, when an axial force is exerted by the push stylet 16, the web 384 breaks or is dislodged, permitting the seeds 50 to be pushed out of the forward end of the seed carrier 314.

The embodiments of FIGS. 14 and 15 may be constructed as follows. A mandrel is positioned within the tube of the seed carrier 214, 314. The forward end of the mandrel terminates a few milimeters rearward of the forward end of the tube and fits snugly within the tube. When the seed carrier 214, 314 is dipped into a vat of coating material, a thin layer of coating material forms on the surface of the tube. Coating material enters the forward end of the tube but is kept from filling the entire tube by the presence of the mandrel. When the seed carrier 214, 314 is removed from the coating material, capillary action and surface tension cause a small quantity of coating material to remain within the forward end of the tube.

Depending upon the viscosity of the material, the coating material may either form a bead 282 (FIG. 14) or a web 384 (FIG. 15) which completely closes off the forward end of the tube.

Referring now to FIGS. 16–19, the concept of a seed-carrying tube having a portion of reduced diameter to prevent the seeds from falling out of the forward end of the tube under force of gravity can be adapted to a conventional two-piece brachytherapy needle assembly 410, where the seeds and spacers are loaded directly into the forward end of a cannula 411 without the use of a separate seed carrier. The cannula 411 includes a hollow shaft 414, a needle head 416, and a forward end 418. A stylet 412 is telescopically received within the cannula 411 and includes a shaft 420, a needle head 422, and a forward end 424 opposite the end to which the needle head is attached. In such an instance, a portion of reduced diameter can retain the seeds 50 in the forward end of the cannula 411. The approach of FIGS. 14 and 15 is especially advantageous in the context of a two-needle assembly. The cannula 411 must be capable of penetrating the tissues of the patient, and as such the cannula shaft 414 is typically formed out of medical-grade stainless steel, which is not inherently lubricious. A lubricious coating 480 applied to the outer periphery of the cannula shaft 414 will reduce friction between the tissues of the patient and the cannula 411. By permitting coating material 480 to accumulate in the forward end of the lumen of the cannula, a portion of reduced diameter in the form of either a circumferential bead (not shown) or a plug 486 can be provided as described above with respect to FIGS. 14 and 15.

Referring again to the three-piece needle assembly of FIGS. 1–15, while the disclosed embodiment employs a friction fit between the needle head 22 of the cannula 12 and the seed carrier 14 to retain the two components stationary relative to one another when the cannula is in its extended (FIG. 10) or retracted (e.g., FIG. 11) position, means other than a friction fit can be employed. For example, a mechanical detent or a latch arrangement can be provided to affirmatively lock the cannula 12 in its extended or retracted positions relative to the seed carrier 14.

Finally, it will be understood that the preferred embodiment has been disclosed by way of example, and that other modifications may occur to those skilled in the art without departing from the scope and spirit of the appended claims.

What is claimed is:

1. A needle for implanting seeds within the body of a patient, comprising:

a hollow cannula having a forward end and a length;

a hollow tube having at least a portion thereof comprised of a transparent material, said hollow tube being telescopically received within said hollow cannula, and said hollow tube having a length greater than said length of said hollow cannula, such that when said hollow cannula is telescopically retracted with respect to said hollow tube, a forward portion of said hollow tube extends beyond said forward end of said hollow cannula; and a stylet telescopically received within said hollow tube;

whereby when seeds and associated spacers are loaded into said tube, proper loading of said seeds and spacers can be visually verified through said portion of said tube which is comprised of said transparent material.

2. The needle of claim 1, wherein said entire tube is comprised of a transparent material.

3. The needle of claim 1, wherein said hollow tube is comprised of a transparent thermoplastic material.

4. The needle of claim 1, wherein said hollow tube is comprised of a lubricious material.

5. The needle of claim 1, wherein said hollow tube further comprises:

an exterior surface, and a lubricious coating on said exterior surface of said hollow tube.

6. The needle of claim 1, wherein said hollow cannula has a cutting edge at a forward end thereof, wherein said hollow tube has a blunt forward end, and wherein said cannula and tube are dimensioned such that when said cannula is withdrawn with respect to said tube, said blunt forward end of said tube extends beyond said cutting edge of said hollow cannula, thereby preventing accidental needle sticks.

7. The needle of claim 1, wherein at least said forward portion of said hollow tube is comprised of a material which is transparent to ultrasound.

8. The needle of claim 7, wherein said forward portion of said hollow tube is of sufficient length to contain said seeds and spacers therewithin such that when said hollow cannula is retracted with respect to said hollow tube and said forward portion of said hollow tube extends beyond said forward end of said hollow cannula, said seeds and spacers are disposed beyond said forward end of said hollow cannula, whereby when said hollow cannula the location of said seeds can be confirmed by ultrasound.

9. A needle for implanting seeds within the body of a patient, comprising:

a hollow cannula;

a hollow tube having a forward end, said hollow tube being telescopically received within said hollow cannula, and said hollow tube comprising a portion of reduced inner diameter adjacent said forward end, whereby when radioactive seeds and associated spacers are loaded into said tube, said portion of reduced inner diameter prevents said seeds from falling out of said forward end of said tube; and a stylet telescopically received within said hollow tube.

10. The needle of claim 9, wherein said portion of reduced inner diameter of said hollow tube comprises an inwardly projecting circumferential lip at said forward end, whereby when radioactive seeds and associated spacers are loaded into said tube, said lip prevents said seeds from falling out of said forward end of said tube.

11. The needle of claim 9, wherein said portion of reduced inner diameter of said hollow tube comprises a inwardly projecting circumferential lip adjacent said forward end, whereby when radioactive seeds and associated spacers are loaded into said tube, said lip prevents said seeds from falling out of said forward end of said tube.

12. The needle of claim 9, further comprising a lubricious coating material disposed on an exterior surface of said hollow tube, and wherein said portion of reduced inner diameter of said hollow tube comprises an accumulation of said coating material on the inner surface of said hollow tube adjacent said forward end thereof, said accumulation of coating material being sufficient to reduce the inner diameter of said hollow tube so as to prevent radioactive seeds within said tube from falling out of said forward end of said tube under force of gravity.

13. The needle of claim 12, wherein said accumulation of coating material forms a membrane which closes off said forward end of said hollow tube.

14. A needle for implanting seeds within the body of a patient, comprising:

a hollow tube; and a stylet telescopically received within said hollow tube;

said hollow tube having a lumen dimensioned to receive radioactive seeds therewithin, and said hollow tube having a constriction at a forward end thereof to prevent said radioactive seeds from exiting said forward end of said tube under force of gravity, and said constriction being deformable under a force in excess of said force of gravity to permit said seeds to pass.

15. The needle of claim 14, further comprising a hollow cannula, said hollow tube being telescopically received within said hollow cannula.

16. The needle of claim 14, wherein said constriction comprises an inwardly projecting lip.

17. The needle of claim 14, wherein said constriction is formed integrally with said hollow tube.

18. The needle of claim 14, wherein said hollow tube is comprised of a flexible thermoplastic material.

19. The needle of claim 14, wherein said hollow tube further comprises an outer surface and a lubricious coating on said outer surface.

20. A needle for implanting radioactive seeds within the body of a patient, comprising:

a hollow cannula;

a hollow tube having a lubricious exterior surface, said hollow tube being telescopically received within said hollow cannula; and a stylet telescopically received within said hollow tube;

whereby when seeds and associated spacers are loaded into said hollow tube, said tube is introduced into a patient, and said tube is withdrawn while said stylet is held steady to push said seeds out into the tissues of said patient, said lubricious coating reduces friction between said tube and the tissues of said patient to minimize displacement of said tissues.

21. A needle for implanting radioactive seeds within the body of a patient, comprising:

a hollow cannula having a cutting forward edge; and a hollow tube having a blunt forward edge, said hollow tube being telescopically received within said hollow cannula;

said cannula and tube being dimensioned such that when said cannula is withdrawn with respect to said tube, said blunt forward edge of said tube extends beyond said cutting edge of said hollow cannula, thereby preventing accidental needle sticks.

22. The needle of claim 21, further comprising a stylet telescopically disposed within said hollow tube.

23. A needle for implanting seeds within the body of a patient, comprising:

a hollow cannula having an exterior surface, a forward end, and a cutting edge at said forward end;

a stylet telescopically received within said hollow tube; and a lubricious coating material disposed on said exterior surface of said cannula and within said forward end of said hollow cannula in an amount sufficient to reduce the internal diameter of said cannula adjacent said forward end such that a seed disposed within said cannula cannot fall out of said forward end of said cannula under force of gravity.

24. The needle of claim 23, wherein said lubricious coating within said forward end of said hollow cannula closes off said forward end of said cannula.

* * * * *